United States Patent [19]
Marconet

[11] Patent Number: 5,399,007
[45] Date of Patent: Mar. 21, 1995

[54] MEDICAL TREATMENT CABINET

[75] Inventor: Robert E. Marconet, Cincinnati, Ohio

[73] Assignee: Reliance Medical Products, Inc., Mason, Ohio

[21] Appl. No.: 47,801

[22] Filed: Apr. 15, 1993

[51] Int. Cl.[6] .............................................. A47B 81/00
[52] U.S. Cl. ................. 312/209; 312/249.8; 312/223.1; 128/630; 607/2
[58] Field of Search ............... 312/209, 249.8, 249.11, 312/223.5, 223.1; 128/630, 633; 607/2

[56] References Cited
U.S. PATENT DOCUMENTS

| | | |
|---|---|---|
| 3,041,957 | 7/1962 | Liptay . |
| 3,547,505 | 12/1970 | Ott et al. ............................ 312/209 |
| 3,724,931 | 4/1973 | Nevyas et al. . |
| 3,969,006 | 7/1976 | Brown . |
| 3,997,218 | 12/1976 | Wolf et al. . |
| 4,002,382 | 1/1977 | Wolf et al. . |
| 4,095,859 | 6/1978 | Decker et al. . |

OTHER PUBLICATIONS

Brochure, "DMI Ex-100 Series Treatment Cabinets", Sep. 1990.

Primary Examiner—Edward K. Look
Assistant Examiner—Hoang Nguyen
Attorney, Agent, or Firm—Wood, Herron & Evans

[57] ABSTRACT

A medical treatment cabinet having a top work surface and a supply stand extending upwardly from the rear of the top surface. The top drawer of the cabinet has a control panel on its from face for operating various electric examination and treatment equipment. The control panel includes connectors and controls for operating fiber optic instruments and the top drawer contains the control box for the fiber optic instruments and the cabinet power box. One or more electric heating units are mounted above a second drawer for warming instruments contained in the drawer. A lower compartment houses a pneumatic pressure pump and a pneumatic vacuum pump for applying positive pressure and vacuum pressure to the patient during treatment. A vacuum collection container is pivotally mounted within the lower compartment such that it may be pivoted out of the compartment to be easily removed and replaced with a sterile container. The vacuum hose used in treating the patient is removably attached to the outside of the cabinet such that it may also be easily removed and replaced with a sterile hose.

34 Claims, 3 Drawing Sheets

MEDICAL TREATMENT CABINET

BACKGROUND OF THE INVENTION

The present invention generally relates to medical treatment cabinets and more specifically to ear, nose and throat (ENT) treatment cabinets used by medical professionals during the examination and treatment of their patients.

Medical treatment cabinets of various designs have been manufactured for many years to give medical personnel in diverse fields of medicine ready access to the instruments and supplies necessary to examine and treat their patients. These medical cabinets have included those shown and described in U.S. Pat. Nos. 3,041,957; 3,724,931; 3,969,006; 3,997,218; 4,002,382; and 4,095,859.

One generally pertinent medical treatment cabinet is disclosed in U.S. Pat. No. 3,969,006 to Brown. Brown discloses a mobile medical emergency cabinet having medications, supplies and equipment visibly displayed to facilitate use in emergency situations. Brown uses a color coding system as one means to facilitate more efficient emergency situation treatments.

In the past, medical treatment cabinets have also included instruments utilizing light sources. For example, U.S. Pat. No. 4,095,859 discloses a portable eye examination system cart including several ophthalmic instruments and a power source for operating the instruments. These instruments are automatically switched on when they are removed from their respective holders and switched off when they are replaced in the holders. The instruments include, for example, a direct ophthalmoscope, a transilluminator, an indirect ophthalmoscope, and a slit-lamp.

It is also generally known to include a vacuum pump as well as a positive pressure pump in such medical treatment cabinets to supply positive pressure and vacuum pressure to flexible hoses which may be connected to nozzles. The nozzles may then be used to direct the appropriate pressure when treating the patient. For example, a nozzle attached to the end of a hose drawing negative pressure may be placed in a patient's mouth during a dental procedure to aspirate the saliva and other material generated during the procedure. The aspiration or vacuum system is usually unregulated and will include a filtered collection container which must be appropriately discarded as it becomes filled with waste material.

As the field of fiber optics has been applied to the medical profession, fiber optical instruments have begun to replace bulkier instruments having built-in light sources. Past medical treatment cabinets have not provided adequately for the use of more efficient fiber optic instrumentation.

Also, past medical treatment cabinets lack an organized method of holding supplies and instruments at the user's disposal while still maximizing the work space on the top surface of the cabinet and keeping heat sensitive chemicals at a safe distance from heat sources contained in and/or on the cabinet.

Moreover, cabinets currently incorporating a vacuum pressure supply system suffer from the disadvantage that it is very cumbersome to change the collection container located in the bottom of the cabinet. The collection containers often have to be disposed of and replaced one or more times during a typical day. In a similar vein, prior cabinets also fail to provide for easy disposal of the flexible vacuum hose that has been exposed to the patient during a medical procedure. Under current guidelines, these hoses must be replaced after use on each patient.

SUMMARY OF THE INVENTION

A preferred embodiment of the present invention is directed to a mobile medical treatment cabinet having a top working surface, a plurality of drawers opening in the front of the cabinet and a lower compartment housing the pumps and containers associated with the positive and negative or vacuum pressure supply system. A stand for holding supplies such as medicines, instruments, tissues and surgical gloves extends upwardly from the rear of the top working surface. The top drawer contains a power control box for operating the various electric instruments and pumps associated with the medical treatment cabinet and a separate box to generate light for fiber optical instruments. Fiber optical instruments are thus easily connected to the front of the cabinet and the fiber optical light sources are easily accessed and replaced when necessary.

The medical treatment cabinet may include a conventional sterilizer unit and an instrument recharging unit for holding and recharging standard battery-operated instruments. Both of these units are preferably recessed in the top surface of the cabinet. The supply stand extending from the top surface of the cabinet preferably includes at least one hollow section for holding, e.g., a tissue dispenser box and a surgical glove dispenser box. The top of the supply stand includes a tray having recesses and/or holes for holding medicine bottles, instruments, etc. The shape and design of the tray serve to maximize the available work surface on the top of the cabinet while keeping the cabinet sufficiently small and portable. The tray is raised above the top working surface of the cabinet a distance sufficient to prevent the heat generated by the electrical equipment in the cabinet from causing deterioration of the chemicals contained in the medicine bottles.

The front surface of the top drawer includes a control panel preferably including the cabinet power switch, a series of indicator lights, power switches for the vacuum and positive pressure pumps, two fiber optical instrument connectors, and two control knobs for varying the intensity of the light transmitted to each fiber optical instrument. As previously mentioned, the top drawer conveniently contains the electrical control box for the cabinet and the fiber optical instrument control box having light bulbs operatively connected to the fiber optical instrument connectors on the drawer front. When the drawer is open, the electrical control box and fiber optic control box are easily accessible for purposes of making necessary repairs such as changing burned out light bulbs. The fiber optical instrument control box also includes a fan which forces heat generated by transformers and light bulbs through an exhaust conduit leading to the rear of the cabinet. The top drawer further includes a hidden latch release button for impeding unauthorized personnel and children from reaching the electrical controls contained therein.

Another drawer contains trays for holding the various instruments to be used to examine and/or treat the patient. One or more electric heating pads are mounted above the instrument trays to warm the instruments to a temperature of about 120° F. so that they may be comfortably used on the patient. This drawer is similar in concept to that disclosed in U.S. Pat. No. 4,910,386 issued to Johnson and assigned to the assignee of the present invention. Additional storage drawers are located below the instrument warming drawer.

A lower compartment having a drop front door houses a vacuum pump and a positive pressure pump for operating suction and positive pressure hoses used while treating the patient. A flexible hose is connected between the vacuum pump and a filtered collection container also located in the lower compartment. Another flexible hose is connected between the collection container and a connector extending between the inside and outside surface of a side wall of the cabinet. A disposable flexible hose is connected to the outside portion of the connector and may be quickly disconnected, discarded and replaced with a sterile hose after use on each patient.

The collection container collects the fluids and other material which have been aspirated from the patient during treatment and filters the collected air before it enters the pump. The vacuum collection container is removably attached to a base which is pivotally mounted to the floor of the lower compartment. The drop front door preferably opens into a horizontal position and the base may be pivoted out of the compartment over the inside surface of the drop front door. In this position the collection container may be easily removed from the base and replaced by a sterile container.

In a manner similar to the vacuum pressure system, a positive pressure pump is connected in a conventional manner to a regulating and filtering container and a flexible hose which is used to direct air pressure at the patient. As mentioned above, switches are located on the control panel of the top drawer's front surface for operating both the vacuum pump and the positive pressure pump.

Other advantages of the invention will be readily apparent to those of ordinary skill in the art from the following detailed description taken in conjunction with the accompanying drawings.

DETAILED DESCRIPTION OF THE PREFERRED EMBODIMENT

Figure 1:
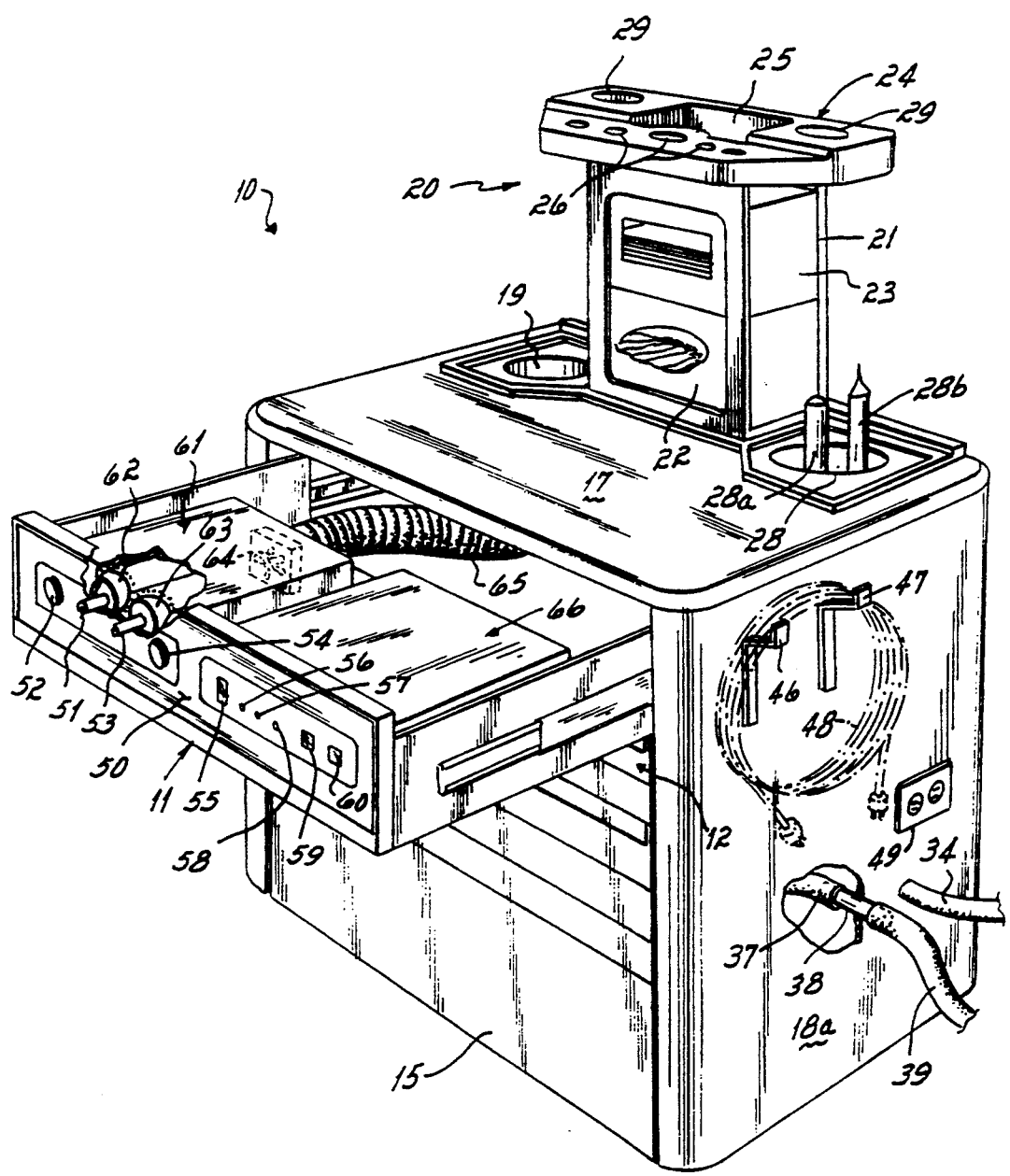
FIG. 1 is a perspective view of the medical treatment cabinet of the invention with the top drawer opened to show the fiber optic and electrical control boxes.
Figure 2:
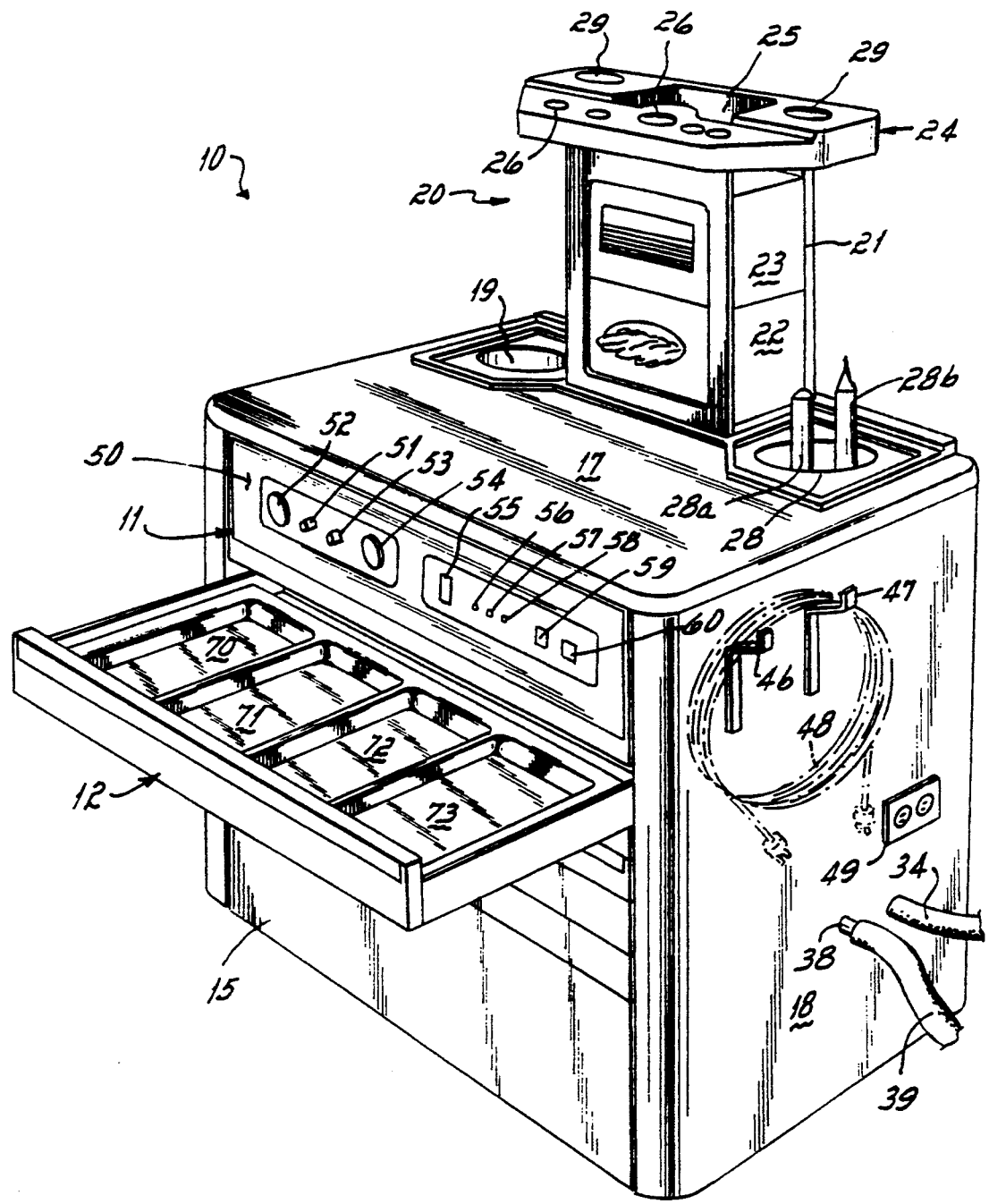
FIG. 2 is a perspective view of the medical treatment cabinet of the invention with the instrument warming drawer opened to show the instrument trays; and, FIG. 3 is a cross sectional side view of the cabinet taken along line 3—3 of FIG. 2 with the bottom front panel lowered to show the pivotally mounted vacuum collection container.
Figure 3:
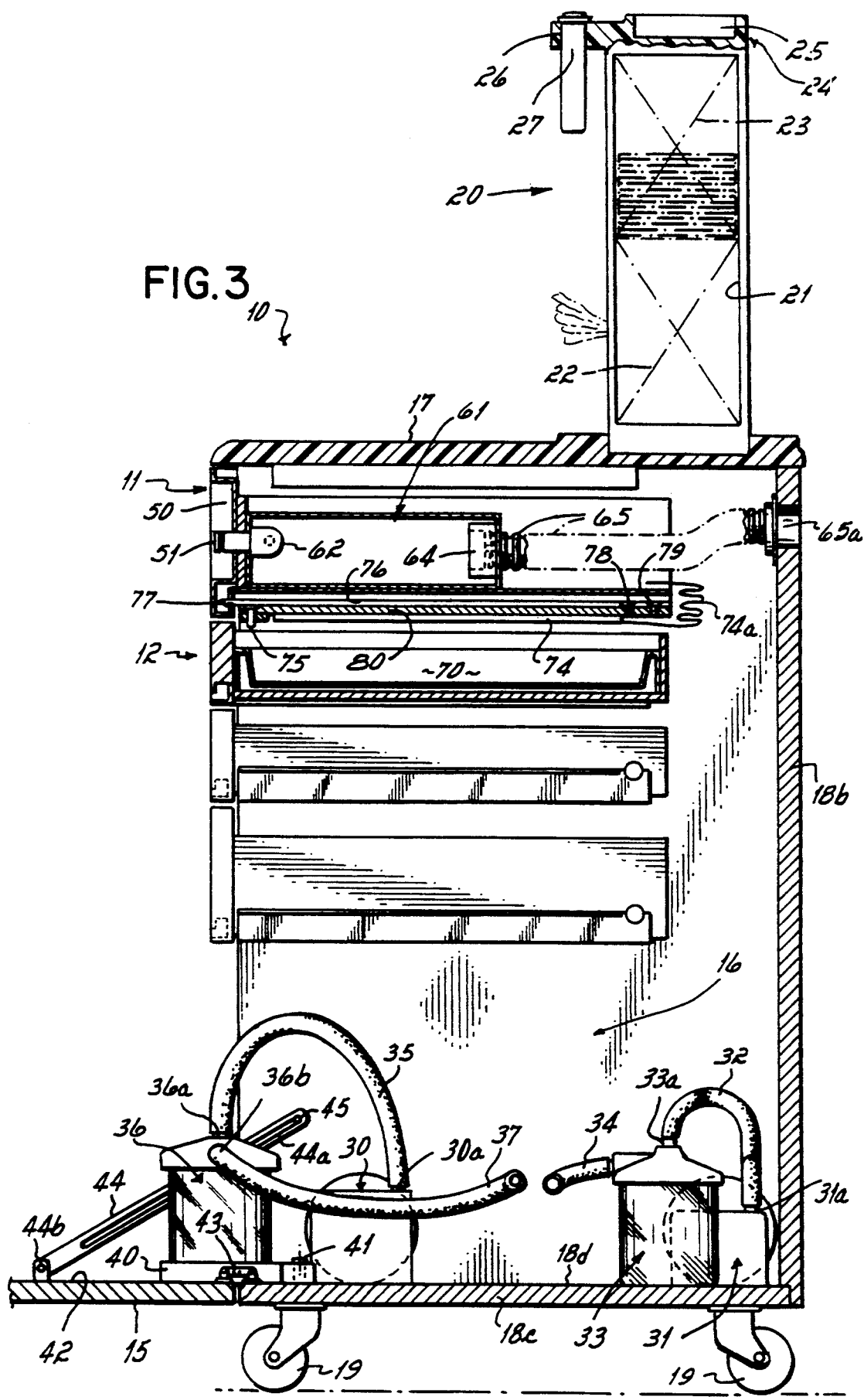

Referring first to FIGS. 1 and 2, a preferred embodiment of the invention includes a cabinet structure 10 having a top work surface 17. A supply stand 20 extends approximately 12-14 inches upward from the rear of the work surface 17 and includes a hollow central space 21 configured to hold, for example, a standard sized tissue dispensing box 22 and surgical glove dispensing box 23. The supply stand 20 further includes an upper tray 24 for holding containers, instruments, and medications conveniently at the disposal of the user. The upper tray 24 preferably includes a central recess 25 for holding instruments or other supplies as desired by the user. The tray 24 also contains two circular recesses or openings 29 on opposite sides of the central recess 25 which may be used to accommodate bottles or cups according to the needs of the user. A front portion of the tray 24 includes several circular holes 26 for holding bottles or containers 27 of medication, anaesthetic, ointment, etc. (as shown in FIG. 3) according to the needs of the user.

Conventional battery-operated instruments 28a, 28b and a glass bead sterilizer 19 are also included behind the work surface 17 on opposite sides of the supply stand 20. The location of the supply stand 20, sterilizer 19 and instruments 28a, 28b at the rear of the work surface 17 serves to maximize the size of the user's working space. The sterilizer 19 is a conventional glass bead sterilizer in which the glass beads are heated to a temperature of approximately 400° F. The instruments 28a, 28b may be of the type commonly used to examine the eyes, ears and/or nose of the patient. The instruments 28a, 28b are powered by rechargeable batteries and are held in a recessed battery recharger 28.

The design of the supply stand 20 prevents heat generated by the sterilizer 19 and the other electrical equipment in the cabinet (to be described below) from adversely affecting the chemicals contained in the medicine bottles, containers, syringes, etc., held in the upper tray 24. That is, by raising these chemicals significantly above the work surface 17, the heat generated by this equipment will dissipate before it can reach and adversely affect the chemicals. Furthermore, the tissue box 22 and surgical glove box 23 provide an insulating effect by absorbing heat as it rises from the cabinet.

In FIG. 1 the top drawer 11 of the cabinet 10 is shown in an open position to show its contents which include a fiber optical instrument control box 61 and the electric control box or power box 66. The front face of the top drawer 11 includes a control panel 50 having controls, connectors, and indicator lights operatively connected to the fiber optical instrument control box 61 and power box 66. On the side of the control panel 50 in front of the fiber optical instrument control box 61 a pair of female connectors 51, 53 extend outwardly from the control box 61 through the drawer front with each connector 51, 53 being adapted to receive the male connector of a fiber optical instrument. Light bulbs 62, 63 are contained in the fiber optical instrument control box 61 for supplying light to the fiber optical instruments through the connectors 51, 53. Control knobs 52, 54 are provided to individually adjust the intensity of the light supplied to each instrument through the connectors 51, 53. The instrument attached to connector 51 is controlled by knob 52 and the instrument attached to connector 53 is controlled by knob 54.

An electric fan 64 is mounted at the rear of the fiber optical instrument control box 61 to vent the heat generated by the light bulbs 62, 63. An exhaust conduit 65 is mounted between the fan 64 and an exhaust opening 65a in the rear face 18b of the cabinet 10 as shown in FIG. 3.

The fiber optic connectors, light sources, and controls used in the present invention are conventional and commercially available and therefore need not be further discussed. The specific fiber optical instrument controls, including the light sources, connectors and fan may be chosen according to the instrument needs of the user.

The control panel 50 further includes a number of switches and indicator lights located on the side of the control panel 50 in front of the power box 66. These switches include a main power switch 55 and switches 59, 60 for operating the vacuum pump 30 and positive pressure pump 31 located in the lower compartment 16 of the cabinet 10 which are described below in connection with FIG. 3. One indicator light 56 is provided to indicate when the sterilizer 19 is in use and two respective indicator lights 57, 58 are provided to indicate when the batteries in the two instruments 28a, 28b are being recharged.

Electric power is supplied to the power box 66 from a standard wall outlet supplying 110/120 Volts A.C. through an electric cord 48 connected between the wall outlet and an outlet 49 in the side wall 18a of the cabinet 10. The power box 66 converts the wall current, as necessary, into forms suitable for running the various electrical equipment of the cabinet 10. The components contained within the power box 66 which are necessary to make such power conversions are well known and conventional and will depend on the specific electrical requirements of the equipment used in the cabinet 10. The power cord 48 may be conveniently stored on brackets 46, 47 attached to the side 18a wall of the cabinet 10 when the cabinet 10 is not being used for an extended period of time. The brackets 46, 47 may also be used to hold other items conveniently at the disposal of the user as well.

As best illustrated in FIG. 3, a child-proof latch mechanism for the top drawer 11 is provided to prevent children from opening the drawer and being exposed to the electrical control boxes 61, 66. The latch includes a latch button 75 which is connected to a flexible bar 76 having a notched free end 77. The notched end 77 locks onto an aperture located on the inside edge of the top drawer 11. The opposite end of the flexible bar 76 is rigidly secured by screws 78, 79 to the top surface of a panel 80 mounted above the second drawer 12 within the cabinet 10. To unlatch the top drawer 11, the user first opens the second drawer 12 then pushes the latch button 75 up to move the notched free end 77 of the bar 76 away from the inside edge of the top drawer 11. This unlocks the notched end 77 from the inside edge of the top drawer 11 and allows the user to pull the top drawer 11 open. When the top drawer 11 is then closed by the user, the notched free end 77 of the flexible rod latches onto the inside edge of the drawer 11 to again lock the drawer in a closed position.

In FIG. 2 the cabinet 10 is shown with a second, instrument warming drawer 12 opened to expose four instrument trays 70, 71, 72, 73. Instruments appropriate to the intended use of the cabinet 10 are kept on these trays and are warmed by one or more electric heating pads 74 as shown in FIG. 3. The heating pads 74 are connected to a suitable power source (e.g., the power box 66) by an expansible coiled wire lead 74a. Preferably, the heating pads 74 consist of 40 W pads capable of warming the instruments contained on the trays 70, 71, 72, 73 to a temperature of approximately 120° F. Thus warmed, the instruments may be used during examinations and treatments, as the case may be, without discomfort to the patient. There may be separate switches provided on the control panel 50 for operating the heating pads 74 or the pads 74 may be operably connected to the main power switch 55 such that they operate whenever the cabinet power supply is switched on.

As further shown in FIG. 3, pneumatic pumps consisting of a vacuum pump 30 and a positive pressure pump 31 are mounted on the floor 18d of the lower compartment 16 of the cabinet 10. The positive pressure supply system is a conventional, regulated air supply system consisting of a pump 31 having a flexible hose 32 connected between an outlet 31a of the pump 31 and the inlet 33a of a regulation container 33. The container 33 includes a filter (not shown) for removing contamination in the air from the pump 31 before it reaches the patient. Another flexible hose 34 is connected to an outlet 33b of the container 33 and leads out of the cabinet 10 through a side wall 18a (as shown in FIG. 1) to be utilized by a medical profession during the treatment of a patient.

The vacuum supply system preferably includes a conventional pneumatic vacuum pump 30 with a flexible hose 35 connected between an air inlet 30a of the pump 30 and the outlet 36a of a collection/filtering container 36. Another flexible hose 37 is connected between the inlet 36b of the container 36 and a connector 38 extending between the inside of the cabinet 10 and the outside of the cabinet 10 through the side wall 18a (see FIG. 1).

As shown in FIG. 1, a disposable flexible vacuum hose 39 is then connected to the outside portion of the connector 38, preferably by a simple frictional fit over the connector 38. Thus, the outside hose 39 may be easily discarded and replaced after it has been exposed to a patient during examination and/or treatment. Current OSHA guidelines require that such vacuum hoses be replaced after use on each patient.

The positive pressure hose 34 may optionally be designed for use with a connector similar to the connector 38 used with the vacuum hose 39. However, current government regulations do not require frequent replacement of positive pressure hoses as they do with vacuum hoses. Therefore, the positive pressure hose 34 has been shown in its conventional form.

Referring again to FIG. 3, the vacuum collection/filtering container 36 is removably attached to a base 40 preferably by being received in a recess (not shown) in the base 40. This allows the user to easily remove and replace the container 36 after each patient. To facilitate easy removal of the container 36 from the lower compartment 16, the lower compartment 16 includes a drop front panel 15 which is attached to the bottom panel 18c of the cabinet 10 by hinges 43 and to the side panels 18a by slotted, pivotal support brackets 44. Although only one hinge 43 and one support bracket 44 are shown in FIG. 3, it will be appreciated that two hinges 43 and two support brackets 44 are actually used, with one of each being located at each end of the drop front panel 15.

The hinges 43 and support brackets 44 allow the panel 15 to be lowered into a horizontal position such that the inside surface 42 of the panel 15 is approximately even or flush with the inside surface 18d of the bottom cabinet panel 18c. In this regard, a slot 44a in each support bracket 44 receives a pin 45 which is rigidly attached to a side wall 18a of the cabinet 10. One end of each support bracket 44 is connected to the inside surface 42 of the panel 15 at a pivot 44b. Thus, as shown in FIG. 3, the panel 15 may be lowered into a horizontal position and held in place by support brackets 44 which slide along the respective pins 45 until each pin 45 reaches the end of its respective slot 44a.

Alternatively, the support brackets 44 may be two-piece units hinged at a midpoint. In either case, a suitable latch mechanism (not shown), such as a magnetic latch, may be provided at the top of the drop front panel 15 to hold the panel 15 in a closed position or, alternatively, the hinge mechanisms may be spring loaded.

The collection container base 40 is mounted to the inside surface 18d of the bottom cabinet panel 18c at a single pivotal fastener 41. The fastener 41 is pivotal about a vertical axis such that the base 40 and its attached collection container 36 may be pivoted out of the lower compartment 16 and over the inside surface 42 of the panel 15 as shown in FIG. 3. Once the container 36 is moved to this outside position it may be easily removed from the base 40 and replaced by a sterile container.

Finally, as also shown in FIG. 3 casters 19 are mounted on the bottom surface of the cabinet 10 to allow the cabinet 10 to be easily moved about by the user or other personnel.

Accordingly, the present invention provides a medical treatment cabinet in which fiber optical instruments may be easily connected to the front of the cabinet and in which the controls associated with the fiber optic system and the cabinet power supply system may be easily accessed and replaced or repaired when necessary.

The invention further provides an instrument warming drawer capable of warming a large number of instruments prior to their use on a patient. Use of the instrument warming drawer further prevents burning the patient with instruments warmed in a conventional sterilizer where temperatures approach 400° F.

Further advantages are realized from the supply stand extending from the top of the cabinet since increased work space is created on the top surface of the cabinet and heat sensitive chemicals are kept in a location which is convenient to the user yet remote from the damaging heat radiating from the equipment in the cabinet.

Finally, the invention provides for an easy method of removing and replacing both the vacuum collection container located within the cabinet and the vacuum hose extending from the cabinet after treating each patient.

Although a preferred embodiment of the invention has been described, certain modifications will become readily apparent to those of ordinary skill in the art without departing from the scope of the invention and applicant intends to be bound only by the scope of the claims appended hereto.

I claim:

1. A cabinet assembly for use during medical operations utilizing fiber optical instruments comprising:
   a cabinet;
   a first drawer slidably received in said cabinet;
   light source means contained within said first drawer for supplying light to fiber optical instruments; and,
   connector means operatively coupled to said light source means for connecting said light source means to a fiber optical instrument.

2. The cabinet assembly of claim 1 wherein said connector means extends through an outside surface of said cabinet.

3. The cabinet assembly of claim 2 wherein said first drawer includes a front surface and said connector means extends through said front surface.

4. The cabinet assembly of claim 1 wherein said light source means comprises at least one light bulb.

5. The cabinet assembly of claim 4 further comprising control means for switching said light bulb on and off and for controlling the intensity of the light produced by said light bulb.

6. The cabinet assembly of claim 5 wherein said control means includes at least one control knob for each light bulb on a front surface of said first drawer.

7. The cabinet assembly of claim 1 further including cooling means contained within said cabinet for dissipating heat from said cabinet.

8. The cabinet assembly of claim 7 wherein said cooling means is a fan contained in said first drawer.

9. The cabinet assembly of claim 8 further including a second drawer for holding medical instruments and having heating means for warming said medical instruments.

10. The cabinet assembly of claim 1 wherein said first drawer contains a power control box for controlling the power used to operate electric equipment connected to the cabinet.

11. The cabinet assembly of claim 10 wherein said first drawer is held in a closed position by hidden latch means for impeding children and unauthorized persons from opening said first drawer.

12. The cabinet assembly of claim 1 further comprising roller means connected to the bottom of said cabinet assembly for allowing movement of said cabinet assembly along a support surface.

13. A cabinet assembly for use during medical operations involving the use of suction instruments comprising:
   a cabinet;
   a compartment contained within said cabinet;
   a collection container assembly including a container and pivotal mounting means for mounting said container within said compartment so as to allow said container to be pivoted at least partially out of said compartment for replacement.

14. The cabinet assembly of claim 13 wherein said container includes an inlet port and an outlet port, said inlet port being connected to a first end of a first vacuum hose and said outlet port being connected to a source of vacuum pressure.

15. The cabinet assembly of claim 14 further comprising:
   vacuum hose connector means attached to a wall of said cabinet such that a first end of said connector means extends inside said wall and a second end of said connector means extends outside said wall and a second end of said first vacuum hose is connected to said first end of said connector means; and,
   a second vacuum hose connected to said second end of said connector means.

16. The cabinet assembly of claim 14 wherein said vacuum source further comprises a pneumatic vacuum pump contained in said compartment.

17. The cabinet assembly of claim 13 further comprising:
   a front panel for enclosing said compartment, said front panel connected to said cabinet by hinge means for allowing said front panel to be pivoted downwardly to an horizontal open position,
   wherein said collection container assembly is pivotable at least partially out of said compartment and over an inside surface of said front panel when said front panel is in said open position.

18. The cabinet assembly of claim 17 wherein said vacuum bottle assembly further comprises:
   a base member pivotally attached to said cabinet for movement between a first position in which said base member is completely contained within said compartment and a second position in which said base member is located at least partially out of said compartment; and, means for removably attaching said container to said base member.

19. The cabinet assembly of claim 18 wherein said base member has a bottom surface adapted to be disposed over said inside surface of said front panel when said front panel is in said open position and said base member is in said second position.

20. The cabinet assembly of claim 13 further comprising roller means connected to the bottom of said cabinet assembly for allowing movement of said cabinet assembly along a support surface.

21. A cabinet assembly for use during medical operations involving the use of suction instruments comprising:
   a cabinet;
   vacuum collection means disposed within said cabinet for operating suction instruments used during medical operations, said vacuum collection means operatively connected to stationary connector means attached to an outside wall of said cabinet; and,
   a first vacuum hose removably attachable to a portion of said connector means located outside of said cabinet.

22. The cabinet assembly of claim 21 wherein said vacuum collection means further comprises:
   a vacuum pump housed within said cabinet;
   a collection container housed within said cabinet and having an inlet port and an outlet port;
   first vacuum conduit means attached between said inlet port of said vacuum bottle and said connector means; and,
   second vacuum conduit means attached between said outlet port of said vacuum bottle and said vacuum pump.

23. The cabinet assembly of claim 22 wherein said first and second vacuum conduit means are flexible hoses.

24. The cabinet assembly of claim 21 further comprising roller means connected to the bottom of said cabinet assembly for allowing movement of said cabinet assembly along a support surface.

25. A cabinet assembly for use during medical operations comprising:
   a lower cabinet having a top surface, said lower cabinet having means for generating heat; and,
   a medicament container stand extending upwardly from said top surface and having container holding means for holding medicament containers spaced a distance above said top surface sufficient to cause the temperature of said medicament containers to be substantially unchanged by said heat generating means.

26. The cabinet assembly of claim 25 wherein said container stand extends from a rear edge of said top surface to maximize the working surface area of said top surface.

27. The cabinet assembly of claim 26 wherein said container stand has a lower portion and an upper portion, said lower portion being narrower than said upper portion and said upper portion having said container holding means.

28. The cabinet assembly of claim 27 wherein said lower portion of said container stand includes a hollow central space for receiving medical supply dispensing containers.

29. The cabinet assembly of claim 27 or 28 wherein said upper portion further includes a tray for holding surgical supplies.

30. The cabinet assembly of claim 27 wherein said heat generating means comprises a sterilizing container recessed in said top surface.

31. The cabinet assembly of claim 30 wherein said heat generating means further comprises an instrument warming drawer in said lower cabinet, said instrument warming drawer being operatively coupled to heating means for warming medical instruments contained in said instrument warming drawer.

32. The cabinet assembly of claim 25 further comprising roller means connected to the bottom of said cabinet assembly for allowing movement of said cabinet assembly along a support surface.

33. A cabinet assembly for use during medical operations comprising:
   a cabinet;
   a first drawer slidably received in said cabinet;
   light source means contained within said first drawer for supplying light to fiber optical instruments;
   connector means operatively coupled to said light source for connecting said light source to a fiber optical instrument;
   an instrument warming drawer in said cabinet, said instrument warming drawer being operatively coupled to heating means for warming medical instruments contained in said instrument warming drawer;
   vacuum collection means disposed within said cabinet for operating suction instruments used during medical operations, said vacuum collection means operatively connected to connector means having a portion extending through an outside wall of said cabinet;
   a first vacuum hose removably attachable to said portion of said connector means outside of said cabinet;
   a compartment contained within said cabinet; and,
   a collection container assembly including a container and pivotal mounting means for mounting said bottle within said compartment so as to allow said container to be pivoted at least partially out of said compartment for replacement.

34. A portable cabinet assembly for use during medical operations comprising:
   a cabinet having roller means connected at the bottom thereof for allowing movement of said cabinet along a support surface;
   a first drawer slidably received in said cabinet;
   light source means contained within said first drawer for supplying light to fiber optical instruments;
   connector means operatively coupled to said light source for connecting said light source to a fiber optical instrument;
   an instrument warming drawer in said cabinet, said instrument warming drawer being operatively coupled to heating means for warming medical instruments contained in said instrument warming drawer;
   vacuum collection means disposed within said cabinet for operating suction instruments used during medical operations, said vacuum collection means operatively connected to connector means having a portion extending through an outside wall of said cabinet;

a first vacuum hose removably attachable to said portion of said connector means outside of said cabinet;

a compartment contained within said cabinet; and, a collection container assembly including a container and pivotal mounting means for mounting said bottle within said compartment so as to allow said container to be pivoted at least partially out of said compartment for replacement.

* * * * *